US008796440B2

(12) United States Patent
Yao

(10) Patent No.: US 8,796,440 B2
(45) Date of Patent: Aug. 5, 2014

(54) PROMOTE SYSTEM FOR REGULATABLE GENE EXPRESSION IN MAMMALIAN CELLS

(75) Inventor: Feng Yao, Needham, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 13/392,954

(22) PCT Filed: Aug. 20, 2010

(86) PCT No.: PCT/US2010/046252
§ 371 (c)(1),
(2), (4) Date: Feb. 28, 2012

(87) PCT Pub. No.: WO2011/025717
PCT Pub. Date: Mar. 3, 2011

(65) Prior Publication Data
US 2012/0190106 A1    Jul. 26, 2012

Related U.S. Application Data

(60) Provisional application No. 61/272,193, filed on Aug. 31, 2009.

(51) Int. Cl.
*C07K 14/005* (2006.01)
*C12N 7/00* (2006.01)

(52) U.S. Cl.
USPC ........................................................ 536/24.1

(58) Field of Classification Search
None
See application file for complete search history.

(56) References Cited

U.S. PATENT DOCUMENTS

| 5,770,414 | A  | 6/1998  | Gage et al. |
| 5,917,122 | A  | 6/1999  | Byrne |
| 5,972,650 | A  | 10/1999 | Yao |
| 6,251,640 | B1 | 6/2001  | Yao |
| 6,444,871 | B1 | 9/2002  | Yao |
| 2002/0028484 | A1 | 3/2002 | Yao |
| 2004/0029229 | A1 | 2/2004 | Reeves et al. |
| 2005/0266564 | A1 | 12/2005 | Yao |
| 2008/0008686 | A1 | 1/2008 | Yao |
| 2010/0015687 | A1 | 1/2010 | Yao |

FOREIGN PATENT DOCUMENTS

| WO | WO 94/04672     | 3/1994 |
| WO | WO 2011/079073 A2 | 6/2011 |

OTHER PUBLICATIONS

Kwissa et al., Journal of Molecular Medicine, 2000, vol. 78, pp. 495-506.*
Baron et al., Nucleic Acids Research, 1995, vol. 23, pp. 3605-3606.*
Klucher et al., Journal of Virology, 1989, vol. 63, pp. 5334-5343.*
Ramos et al., Microbiology and Molecular Biology Reviews, 2005, vol. 69, pp. 326-356.*
Armentano et al., Journal of Virology, 1999, vol. 73, pp. 7031-7034.*
International Search Report for PCT/US2010/046252 filed Aug. 20, 2010.
Written Opinion of the International Searching Authority for PCT/US2010/046252 filed Aug. 20, 2010.
International Preliminary Examination Report for PCT/US2010/046252 filed Aug. 20, 2010.
Brinster, et al., "Regulation of metallothionein-thymidine kinase fusion plasmids injected into mouse eggs," *Nature* 296(4):39-42 (Mar. 1982).
Brown, et al., "*lac* Repressor Can Regulate Expression from a Hybrid SV40 Early Promoter Containing a *lac* Operator in Animal Cells," *Cell* 49:603-612 (Jun. 1987).
Deuschle, et al., "Tetracycline-Reversible Silencing of Eukaryotic Promoters," *Mol. Cell. Biol.* 15(4):1907-1914 (Apr. 1995).
Ghosh, et al., "Expanding Adeno-associated Viral Vector Capacity: A Tale of Two Vectors," *Biotechnology and Genetic Engineering Reviews* 24:165-178 (2007).
Hennighausen, et al., "Conditional Gene Expression in Secretory Tissues and Skin of Transgenic Mice Using the MMTV-LTR and the Tetracycline Responsive System," *Journal of Cellular Biochemistry* 59:463-472 (1995).
Hillen, et al., "Mechanisms Underlying Expression of TN10 Encoded Tetracycline Resistance," *Annu. Rev. Microbiol.* 48:345-369 (1994).
Kim, et al., "Tetracycline Repressor-Regulated Gene Repression in Recombinant Human Cytomegalovirus," *Journal of Virology* 69(4):2565-2573 (Apr. 1995).
Klock, et al., "Oestrogen and glucocorticoid responsive elements are closely related but distinct," *Nature* 329(22):734-736 (Oct. 1987).
Labow, et al., "Conversion of the *lac* Repressor into an Allosterically Regulated Transcriptional Activator for Mammalian Cells," *Mol. Cell. Biol.* 10(7):3343-3356 (Jul. 1990).
Le, et al., "Inducible Expression of Cre Recombinase in the Retinal Pigmented Epithelium," *Investigative Ophthalmology & Visual Science* 49(3):1248-1253 (2008).
Nover, in *Heat Shock Response*, pp. 167-220, CRC, Fla. (1991).
Postle, et al., "Nucleotide sequence of the repressor gene of the Tn10 tetracycline resistance determinant," *Nucleic Acids Research* 12(12):4849-4863 (1984).
Radomska, et al., "Transgenic targeting with regulatory elements of the human *CD34* gene," *Blood* 100(13):4410-4419 (Dec. 2002).
Wissmann, et al., "Saturation Mutagenesis of the Tn10-encoded *tet* Operator $O_1$; Identification of Base-pairs Involved in Tet Repressor Recognition," *J. Mol. Biol.* 202:397-406 (1998).

(Continued)

*Primary Examiner* — Anne Gussow
*Assistant Examiner* — Mindy G Brown
(74) *Attorney, Agent, or Firm* — David S. Resnick; Candace M. Summerford; Nixon Peabody LLP

(57) ABSTRACT

The present invention is directed to a bidirectional human cytomegalovirus (hCMV) promoter that can be used to promote transcription on both strands of a double stranded DNA molecule. When used as part of a system that includes tet operator and the gene coding for the tet repressor, the promoter can be used to induce mammalian gene expression in a highly regulated way.

10 Claims, 2 Drawing Sheets

(56) References Cited

OTHER PUBLICATIONS

Yao, et al.,"Tetracycline Repressor, tetR, rather than the tetR-Mammalian Cell Transcription Factor Fusion Derivatives, Regulates Inducible Gene Expression in Mammalian Cells," *Human Gene Therapy* 9:1939-1950 (Sep. 1998).

Baskar, et al., "Developmental Analysis of the Cytomegalovirus Enhancer in Transgenic Animals," *Journal of Virology* 70(5):3215-3226 (May 1996).

Boshart, et al., "A Very Strong Enhancer Is Located Upstream of an Immediate Early Gene of Human Cytomegalovirus," *Cell* 41:521-530 (Jun. 1985).

Foecking, et al., "Powerful and versatile enhancer-promoter unit for mammalian expression vectors," *Gene* 45:101-105 (1986).

Koedood, et al., "Human Cytomegalovirus (HCMV) Immediate-Early Enhancer/Promoter Specificity during Embryogenesis Defines Target Tissues of Congenital HCMV Infection," *Journal of Virology* 69(4):2194-2207 (Apr. 1995).

Schmidt, et al., "The Cytomegalovirus Enhancer: a Pan-Active Control Element in Transgenic Mice," *Molecular and Cellular Biology* 10(8):4406-4411 (Aug. 1990).

Stinski, et al., "Activation of the Major Immediate Early Gene of Human Cytomegalovirus by *cis*-Acting Elements in the Promoter-Regulatory Sequence by Virus-Specific *trans*-Acting Components," *Journal of Virology* 55(2):431-441 (Aug. 1985).

\* cited by examiner

SEQUENCE LISTING

<160> NUMBER OF SEQ ID NOS: 13

<210> SEQ ID NO 1
<211> LENGTH: 755
<212> TYPE: DNA
<213> ORGANISM: Artificial Sequence
<220> FEATURE:
<223> OTHER INFORMATION: Chemically synthesized

<400> SEQUENCE: 1

```
acggttcact aaacgagctc tgcttatata gacctcccac cgtacacgcc taccgcccat      60
ttgcgtcaat ggggcggagt tgttacgaca ttttggaaag tcccgttgat tttggtgtac     120
atttatattg gctcatgtcc aatatgaccg ccatgttgac attgattatt gactagttat     180
taatagtaat caattacggg gtcattagtt catagcccat atatggagtt ccgcgttaca     240
taacttacgg taaatggccc gcctggctga ccgcccaacg acccccgccc attgacgtca     300
ataatgacgt atgttcccat agtaacgcca atagggactt tccattgacg tcaatgggtg     360
gagtatttac ggtaaactgc ccacttggca gtacatcaag tgtatcatat gccaagtccg     420
```

-continued

```
cccctattg acgtcaatga cggtaaatgg cccgcctggc attatgccca gtacatgacc      480
ttacgggact ttcctacttg gcagtacatc tacgtattag tcatcgctat taccatggtg      540
atgcggtttt ggcagtacac caatgggcgt ggatagcggt tgactcacg gggatttcca      600 agtctccacc ccattgacgt caatgggagt tgttttggc accaaaatca acgggacttt      660
ccaaaatgtc gtaataaccc cgccccgttg acgcaaatgg cggtaggcg tgtacggtgg      720 gaggtctata taagcagagc tcgtttagtg aaccg                                755

<210> SEQ ID NO 2
<211> LENGTH: 604
<212> TYPE: DNA
<213> ORGANISM: Human cytomegalovirus

<400> SEQUENCE: 2
catgttgaca ttgattattg actagttatt aatagtaatc aattacgggg tcattagttc       60
atagcccata tatggagttc cgcgttacat aacttacggt aaatggcccg cctggctgac      120
cgcccaacga cccccgccca ttgacgtcaa taatgacgta tgttcccata gtaacgccaa      180
tagggacttt ccattgacgt caatgggtgg agtatttacg gtaaactgcc cacttggcag      240
tacatcaagt gtatcatatg ccaagtccgc cccctattga cgtcaatgac ggtaaatggc      300
ccgcctggca ttatgcccag tacatgacct tacgggactt tcctacttgg cagtacatct      360
acgtattagt catcgctatt accatggtga tgcggttttg gcagtacacc aatgggcgtg      420
gatagcggtt tgactcacgg ggatttccaa gtctccaccc cattgacgtc aatgggagtt      480
tgttttggca ccaaaatcaa cgggactttc caaaatgtcg taataaccc gccccgttga      540 cgcaaatggg cggtaggcgt gtacggtggg aggtctatat aagcagagct cgtttagtga      600
accg                                                                  604

<210> SEQ ID NO 3
<211> LENGTH: 114
<212> TYPE: DNA
<213> ORGANISM: Human cytomegalovirus

<400> SEQUENCE: 3
ccaaaatcaa cgggactttc caaaatgtcg taataaccc gccccgttga cgcaaatggg       60
cggtaggcgt gtacggtggg aggtctatat aagcagagct cgtttagtga accg           114

<210> SEQ ID NO 4
<211> LENGTH: 114
<212> TYPE: DNA
<213> ORGANISM: Artificial Sequence
<220> FEATURE:
<223> OTHER INFORMATION: chemically synthesized

<400> SEQUENCE: 4
cggttcacta aacgagctct gcttatatag acctcccacc gtacacgcct accgcccatt       60
tgcgtcaacg gggcggggtt attacgacat tttggaaagt cccgttgatt ttgg          114

<210> SEQ ID NO 5
<211> LENGTH: 795
<212> TYPE: DNA
<213> ORGANISM: Artificial Sequence
<220> FEATURE:
<223> OTHER INFORMATION: chemically synthesized
```

<400> SEQUENCE: 5

```
gagctcgtcg acgatctcta tcactgatag ggagatctct atcactgata gggagagctc    60
tgcttatata gacctcccac cgtacacgcc taccgcccat ttgcgtcaat ggggcggagt   120
tgttacgaca ttttggaaag tcccgttgat tttggtgtac atttatattg gctcatgtcc   180
aatatgaccg ccatgttgac attgattatt gactagttat taatagtaat caattacggg   240
gtcattagtt catagcccat atatggagtt ccgcgttaca taacttacgg taaatggccc   300
gcctggctga ccgcccaacg accccgccc attgacgtca ataatgacgt atgttcccat   360
agtaacgcca atagggactt tccattgacg tcaatgggtg gagtatttac ggtaaactgc   420
ccacttggca gtacatcaag tgtatcatat gccaagtccg cccccctattg acgtcaatga  480
cggtaaatgg cccgcctggc attatgccca gtacatgacc ttacgggact ttcctacttg   540
gcagtacatc tacgtattag tcatcgctat taccatggtg atgcggtttt ggcagtacac   600
caatgggcgt ggatagcggt ttgactcacg gggatttcca agtctccacc ccattgacgt   660
caatgggagt ttgttttggc accaaaatca acgggacttt ccaaaatgtc gtaataaccc   720
cgccccgttg acgcaaatgg gcggtaggcg tgtacggtgg gaggtctata taagcagagc   780
tcgtttagtg aaccg                                                    795
```

```
<210> SEQ ID NO 6
<211> LENGTH: 40
<212> TYPE: DNA
<213> ORGANISM: Escherichia coli

<400> SEQUENCE: 6
tctctatcac tgatagggag atctctatca ctgatabggga                         40

<210> SEQ ID NO 7
<211> LENGTH: 19
<212> TYPE: DNA
<213> ORGANISM: Escherichia coli

<400> SEQUENCE: 7
tccctatcag tgatagaga                                                 19

<210> SEQ ID NO 8
<211> LENGTH: 29
<212> TYPE: DNA
<213> ORGANISM: Artificial Sequence
<220> FEATURE:
<223> OTHER INFORMATION: chemically synthesized

<400> SEQUENCE: 8
gacttgtaca gttgacattg attattgac                                      29

<210> SEQ ID NO 9
<211> LENGTH: 30
<212> TYPE: DNA
<213> ORGANISM: Artificial Sequence
<220> FEATURE:
<223> OTHER INFORMATION: chemically synthesized

<400> SEQUENCE: 9
gacttgtaca acatctacgt attagtcatc                                     30

<210> SEQ ID NO 10
<211> LENGTH: 30
<212> TYPE: DNA
<213> ORGANISM: Artificial Sequence
```

```
<220> FEATURE:
<223> OTHER INFORMATION: chemically synthesized

<400> SEQUENCE: 10
gacttgtaca tgggagtttg ttttggcacc                                  30

<210> SEQ ID NO 11
<211> LENGTH: 31
<212> TYPE: DNA
<213> ORGANISM: Artificial Sequence
<220> FEATURE:
<223> OTHER INFORMATION: chemically synthesized

<400> SEQUENCE: 11
gacttgtaca ccaaaatgtc gtaacaactc c                                31

<210> SEQ ID NO 12
<211> LENGTH: 29
<212> TYPE: DNA
<213> ORGANISM: Artificial Sequence
<220> FEATURE:
<223> OTHER INFORMATION: chemically synthesized

<400> SEQUENCE: 12
gacttgtaca cagaagccat agagcccac                                   29

<210> SEQ ID NO 13
<211> LENGTH: 16
<212> TYPE: DNA
<213> ORGANISM: Human cytomegalovirus

<400> SEQUENCE: 13
tatataagca gagatc                                                 16
```

PROMOTE SYSTEM FOR REGULATABLE GENE EXPRESSION IN MAMMALIAN CELLS

CROSS REFERENCE TO RELATED APPLICATIONS

This application is a 35 U.S.C. 371 National Stage Application of International Application No. PCT/US2010/046252 filed on Aug. 20, 2010, which designates the United States, and which claims benefit under 35 U.S.C. §119(e) of U.S. Provisional Application No. 61/272,193 filed Aug. 31, 2009, the contents of each of which is incorporated herein by reference in its entirety.

STATEMENT OF GOVERNMENT FUNDING

This invention was made with Government support under Grant No. RO1 AI05088 awarded by the National Institutes of Health. The U.S. Government therefore has certain rights in the invention.

SEQUENCE LISTING

The instant application contains a Sequence Listing which has been submitted in ASCII format via EFS-Web and is hereby incorporated by reference in its entirety. Said ASCII copy, created on Sep. 25, 2013, is named 13392954 and is 5,538 bytes in size.

FIELD OF THE INVENTION

The present invention is concerned with recombinant gene expression in mammalian cells. In particular, it is concerned with bidirectional hCMV promoters and systems that use these promoters for the regulated expression of genes.

BACKGROUND OF THE INVENTION

The ability to promote and regulate recombinant gene expression is of importance in research, in the industrial production of cell products, and in the development of effective approaches to gene therapy. Attempts to regulate gene expression in mammalian cells have generally focused on the use of inducible promoters (Brinster, et al., *Nature* 296:39-42 (1982); Nover, in *Heat Shock Response*, pp. 167-220, CRC, Fla. (1991)); Klock, et al., *Nature* 329:734-736 (1987)) or on the use of prokaryotic regulatory elements (see e.g., Labow, et al., *Mol. Cell. Biol.* 10:3343-3356 (1990); Brown, et al., *Cell* 49:603-612 (1987); Kim, et al., *J. Virol.* 69:2565-2573 (1995); Hennighausen, et al., *J. Cell. Biochem.* 59:463-472 (1995); Deuschle, et al., *Mol. Cell. Biol.* 15:1907-1914 (1995)).

One particularly effective system for regulating gene expression in mammalian cells uses a tetracycline-inducible transcription switch (U.S. Pat. Nos. 6,444,871; 6,251,640; 5,972,650; Yao, et al., *Hum. Gene Ther.* 9:1939-1950 (1998)). Gene expression is suppressed in this system by the binding of the tetracycline repressor, tetR, to a tetracycline operator (tetO) sequence that has been inserted downstream of the TATA element (TATATAA) in an hCMV major immediate-early promoter. In order to turn on expression of the gene sequence, tetracycline is introduced into the system. This enters into cells, binds to the repressor protein and causes it to dissociate from the operator. This system has been used in commercially available plasmids (T-Rex System™, Invitrogen™, Carlsbad, Calif.), in HSV vectors designed to deliver therapeutic genes to cells (US 20050266564) and in oncolytic viruses (US 20080008686).

A problem that has limited the use of the systems described above, particularly in the area of gene therapy, is that the vectors used to deliver recombinant DNA to cells often have a very limited capacity. For example, Adeno-associated viral vectors are among the most promising for gene therapy but can only accommodate a few kilobases of DNA (Ghosh, et al., *Genet. Eng. Rev.* 24:165-178 (2007)). Ways to more efficiently use the space available in such vectors should expand their utility.

SUMMARY OF THE INVENTION

The present invention is based upon the construction and characterization of a bidirectional hCMV immediate-early promoter that can be used either independently or as part of a system for achieving tetracycline-regulatable gene expression in mammalian cells. This system is characterized by a gene of interest that is under control of the bidirectional promoter and which is immediately 3' to the TATA element of the promoter. Expression of tetR may be driven by the same promoter in a reverse orientation (FIG. 2). Using hEGF (human epidermal growth factor) as a reporter gene in plasmid pCEP4-tetR-hEGF-94, it has been found that transient transfection of pCEP4-tetR-hEGF in HeLa, 293T, and Vero cells leads to 100- to 10,000-fold regulation in hEGF expression which is dependent upon the presence or absence of tetracycline.

In its first aspect, the invention is directed to a double stranded DNA molecule characterized by the presence of a bidirectional human cytomegalovirus (hCMV) promoter that is operably linked at either end to a gene. A first gene lies 3' to the promoter on a first strand of DNA and a second gene lies 3' to the promoter in reverse orientation on a second, opposite strand of DNA. As used herein, the term "operably linked" refers to genetic elements that are joined together in a manner that enables them to carry out their normal functions. For example, a gene is operably linked to a promoter when its transcription is under the control of the promoter and this transcription results in the production of the product normally encoded by the gene. A first TATA element of the first promoter is on the first DNA strand and lies 5' to the first gene. A second TATA element of the second promoter is located on the second strand and lies 5' to the second gene on the complementary DNA strand. The term "complementary" as used herein refers to the normal base pairing partner of a given nucleotide. Thus, A is the complementary nucleotide of T and G is the complementary nucleotide of C. A complementary DNA strand (also referred to herein as the "opposite strand") would therefore be a DNA strand that has a sequence of complementary nucleotides oriented in a way that permits the strands to anneal. For example, the complementary strand of 5'-ATCCG-3' would be 3'-TAGGC-5'.

As discussed further below, the bidirectional promoter can be modified by incorporating a tet-operator sequence at one end and used as part of a system that both promotes and regulates gene expression. The tetracycline operator sequence preferably has two op2 repressor binding sites joined together by between two and twenty linking nucleotides and is located between six and twenty-four nucleotides 3' to the last nucleotide in a TATA element in the promoter. In a preferred embodiment, the other end of the bidirectional promoter, i.e., the end that has not been modified by the incorporation of a tet operator sequence, promotes the transcription of a sequence coding for the tet repressor.

The structure of the bidirectional hCMV promoter may be understood by reference to the nucleotide sequence shown below (SEQ ID NO:1). Unless otherwise indicated, all sequences shown herein are read from left to right in the 5' to 3' direction.

(SEQ ID NO: 1)
acggttcactaaacgagctctgc*ttatata*gacctcccaccgtacacgcctaccgcccatttgcgtcaatggggcggagttgttacga cattttggaaagtcccgttgattttggTGTACATTTATATTGGCTCATGTCCAATATGACCGC<u>CAT</u>

<u>GTTGACATTGATTATTGACTAGTTATTAATAGTAATCAATTACGGGGTCATTAGT</u>

<u>TCATAGCCCATATATGGAGTTCCGCGTTACATAACTTACGGTAAATGGCCCGCC</u>

<u>TGGCTGACCGCCCAACGACCCCCGCCCATTGACGTCAATAATGACGTATGTTCC</u>

<u>CATAGTAACGCCAATAGGGACTTTCCATTGACGTCAATGGGTGGAGTATTTACG</u>

<u>GTAAACTGCCCACTTGGCAGTACATCAAGTGTATCATATGCCAAGTCCGCCCCC</u>

<u>TATTGACGTCAATGACGGTAAATGGCCCGCCTGGCATTATGCCCAGTACATGAC</u>

<u>CTTACGGGACTTTCCTACTTGGCAGTACATCTACGTATTAGTCATCGCTATTACC</u>

<u>ATGGTGATGCGGTTTTGGCAGTACACCAATGGGCGTGGATAGCGGTTTGACTCA</u>

<u>CGGGGATTTCCAAGTCTCCACCCCATTGACGTCAATGGGAGTTTGTTTTGGCAC</u>

<u>CAAAATCAACGGGACTTTCCAAAATGTCGTAATAACCCCGCCCCGTTGACGCAA</u>

<u>ATGGGCGGTAGGCGTGTACGGTGGGAGGTCTATATAAGCAGAGCTCGTTTAGTG</u>

<u>AACCG</u>.

The bidirectional promoter comprises the wild type hCMV major immediate-early promoter sequence (shown in capitals and underlined) and a DNA segment complementary to a portion of the 3' end of the wild type promoter that has been ligated to its 5' end (shown as lower case letters above). The TATA element for transcription promoted by the strand above is shown in upper case, italics and bold and the TATA element promoting transcription from the opposite strand in the reverse direction is represented by the lower case letters in italics and bold. The uppercase letters that are not underlined are derived from a vector used in constructing the above sequence and are not critical to promoter activity. It will be understood that this portion of the sequence can be changed, shortened or fully deleted. This portion of the sequence could also be increased but since the objective of this invention is to minimize the size of the promoter, an increase in sequence length in this region is not preferred. The number of nucleotides complementary to the 3' sequence of the wild type hCMV promoter and ligated to its 5' end (i.e., the sequence in lowercase above) should be 29 to 130 nucleotides long, preferably 60 to 120 nucleotides long, 80 to 110 nucleotides long, 94 to 108 nucleotides long and more preferably 94 nucleotides.

The promoter may be viewed as having the structure: X-Y-Z, where Z is the wild type hCMV major immediate-early promoter sequence shown below as consisting of 604 nucleotides 5' to the transcription start site (+1):

(SEQ ID NO: 2)
<u>C</u>ATGTTGACATTGATTATTGACTAGTTATTAATAGTAATCAATTACGGGG

TCATTAGTTCATAGCCCATATATGGAGTTCCGCGTTACATAACTTACGGT

AAAT<u>G</u>GCCCGCCTGGCTGACCGCCCAACGACCCCCGCCCATTGACGTCAA

TAATGACGTATGTTCCCATAGTAACGCCAATAGGGACTTTCCATTGACGT

CAATGGGTGGAGTATTTACGGTAAACTGCCCACTTGGCAGTACATCAAGT

GTATCATATGCCAAGTCCGCCCCCTATTGACGTCAATGACGGTAAATGGC

CCGCCTGGCATTATGCCCAGTACATGACCTTACGGGACTTTCCTACTTGG

-continued
CAGTACATCTACGTATTAGTCATCGCTATTACCATGGTGATGCGGTTTTG

GCAGTACACCAATGGGCGTGGATAGCGGTTTGACTCACGGGGATTTCCAA

GTCTCCACCCCATTGACGTCAATGGGAGTTTGTTTTGGCACCAAAATCAA

CGGGACTTTCCAAAATGTCGTAATAACCCCGCCCCGTTGACGCAAATGGG

CGGTAGGCGTGTACGGTGGGAGGTCTATATAAGCAGAGCTCGTTTAGTGA

ACCG+1

The +1 in the sequence above is the transcription start site and would, if depicted, be T. The wild type sequence shown above extends 604 nucleotides from the start site of transcription in the 3' to 5' direction. However, this entire sequence is not needed for promoter activity. For the purposes of the present application, the wild type hCMV promoter will be considered to include anywhere from 500 to 604 nucleotides 5' to the transcription start site. The underlined G in SEQ ID NO:2 is the 500$^{th}$ nucleotide from the start site of transcription and the C that is underlined and in italics is the 604$^{th}$. Thus, running in the 3' to 5' direction, the promoter would, at a minimum, extend from the start site of transcription (+1) to the underlined G located 500 nucleotides away. It may also extend further in the 3' to 5' direction, following the sequence shown above, as far as the underlined and italicized C located 604 nucleotides away from the start site of transcription.

Y is a linking sequence of 0-200 nucleotides, preferably, 0-100 nucleotides and more preferably, 0-40 nucleotides; and X is a sequence that is complementary to 29-130 consecutive nucleotides at the 3' end of the above wild type sequence and which is added to the 5' end of Y in reverse orientation. For example, the sequence:

(SEQ ID NO: 3)
CCAAAATCAACGGGACTTTCCAAAATGTCGTAATAACCCCGCCCCGTTGA

CGCAAATGGGCGGTAGGCGTGTACGGTGGGAGGTCTATATAAGCAGAGCT

CGTTTAGTGAACCG may be taken from the 3' end of the hCMV wild type sequence and added at the 5' end of Y as:

(SEQ ID NO: 4)
CGGTTCACTAAACGAGCTCTGCTTATATAGACCTCCCACCGTACACGCCT

ACCGCCCATTTGCGTCAACGGGGCGGGGTTATTACGACATTTTGGAAAGT

CCCGTTGATTTTGG.

The most critical thing for X is the inclusion of the TATA element, i.e. the seven nucleotide sequence TATATAA. Thus, as an alternative, X may be obtained by beginning at the A in the TATA element lying furthest 3', i.e. the underlined A above, and moving from 7 to 107 nucleotides in the 3' to 5' direction. Again, this sequence is added to the 5' end of Y reverse orientation The promoter described above may be used to promote the transcription of two different genes, one that is immediately 3' to the X-Y-Z sequence described above (e.g., SEQ ID NO:1) and one that is 3' to the sequence on the complementary DNA strand. If desired, the promoter can be incorporated into viral vectors (e.g., adeno-associated viral vectors) and used to promote gene expression. As will be apparent to one of skill in the art, minor changes and standard modifications can be made to the promoter without affecting its basic design or function.

In a preferred embodiment, the promoter shown above is modified so that the expression of a gene operably linked to the promoter is controlled by the tet operator/repressor elements that have been previously described in the art (see U.S. Pat. Nos. 6,444,871; 6,251,640; 5,972,650; Yao, et al., *Hum. Gene Ther.* 9:1939-1950 (1998), each of which is incorporated by reference herein in their entirety). Using this system, a tet operator (tetO) sequence is incorporated into the promoter between a TATA element (i.e., TATATAA) and the start site of transcription of the gene. In particular, the first nucleotide of the tetO sequence should be between 6 and 24 nucleotides 3' to the TATA element of the promoter. This is illustrated below:

However, up to 100 additional intervening nucleotides may precede the start site of transcription.

In a particularly preferred embodiment, one strand of the bidirectional promoter will have a gene of interest under the control of a tet-O sequence as described above and the other end will be operably linked to a sequence coding for the tet repressor. In terms of the sequence shown above, the tet repressor would be 3' to the wild type sequence terminating in CCGT, and the gene of interest would be coded for on the complementary strand of DNA and be 3' to the sequence shown above as gagc on the complementary strand.

The gene of interest that is operably linked to the bidirectional promoter may be, for example, a gene that promotes the production of a useful product in an industrial setting or a gene whose expression is of interest to a researcher. The gene of interest may also be a gene with potential therapeutic value when delivered to cells either in vitro or in vivo. Examples of genes that could be of interest in this respect include: genes encoding factor VIII, factor IX, β-globin, low-density protein receptor, adenosine deaminase, purine nucleoside phosphorylase, sphingomyelinase, glucocerebrosidase, cystic fibrosis transmembrane regulator, α-antitrypsin, CD-18, omithine transcarbamylase, arginosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase, genes affecting the immune system, tumor suppressor genes, etc.

<u>TAGTAATCAATTACGGGGTCATTAGTTCATAGCCCATATATGGAGTTCCGCGTT</u>

<u>ACATAACTTACGGTAAATGGCCCGCCTGGCTGACCGCCCAACGACCCCCGCCCA</u>

<u>TTGACGTCAATAATGACGTATGTTCCCATAGTAACGCCAATAGGGACTTTCCAT</u>

<u>TGACGTCAATGGGTGGAGTATTTACGGTAAACTGCCCACTTGGCAGTACATCAA</u>

<u>GTGTATCATATGCCAAGTCCGCCCCCTATTGACGTCAATGACGGTAAATGGCCC</u>

<u>GCCTGGCATTATGCCCAGTACATGACCTTACGGGACTTTCCTACTTGGCAGTAC</u>

<u>ATCTACGTATTAGTCATCGCTATTACCATGGTGATGCGGTTTTGGCAGTACACC</u>

<u>AATGGGCGTGGATAGCGGTTTGACTCACGGGGATTTCCAAGTCTCCACCCCATT</u>

<u>GACGTCAATGGGAGTTTGTTTTGGCACCAAAATCAACGGGACTTTCCAAAATGT</u>

<u>CGTAATAACCCCGCCCCGTTGACGCAAATGGGCGGTAGGCGTGTACGGTGGGA</u>

<u>GGTCTATATAAGCAGAGCTCGTTTAGTGAACCG</u>

The sequence shown in lower case and italics above corresponds to the tetO sequence: tctctatcactgatagggagatctctatcactgataggga (SEQ ID NO:6). On the complementary strand, the first nucleotide of this sequence is the tenth nucleotide 3' from the last nucleotide in the TATA element. The gene of interest would preferably begin with the next nucleotide.

known cellular transcription factors are indicated. TetR: tetracycline repressor, tetO: tetracycline operator; hEGF: human epidermal growth factor, SV40-pA; SV40 poly A signal.

Figure 2:
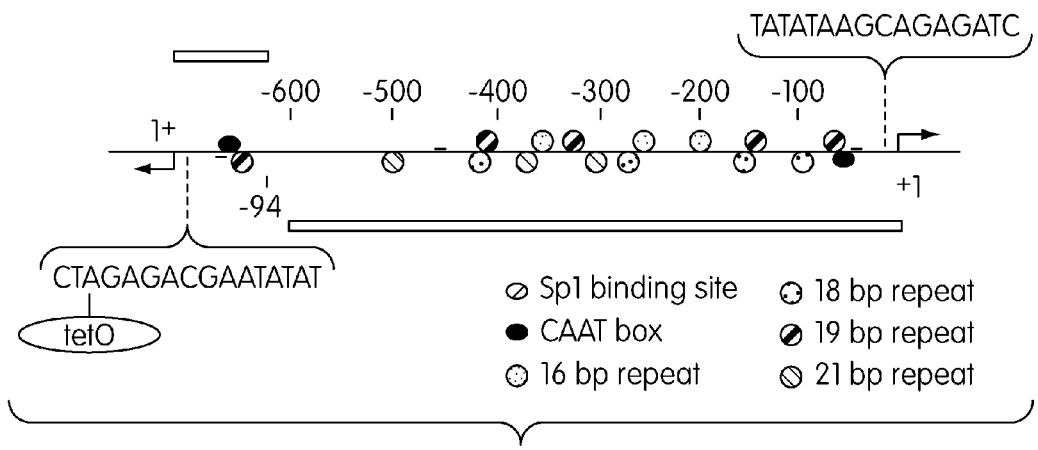

FIG. 2 is a schematic diagram of a single bidirectional hCMV major immediate-early promoter system in pCEP4tetR-hEGF-94. The hCMV major immediate-early promoter TATATAA element containing sequence TATATA AGCAGAGATC (SEQ ID NO:13) is shown for the top and bottom strands. regulation of hEGF expression. Vero cells were transfected with the pCEP4-tetR-hEGF-94. At 4 hours post-transfection, medium was changed either with no tetracycline or with tetracycline at the indicated concentrations for 24 h. Untransfected Vero cells were used as a negative control. Levels of hEGF expression were determined by hEGF-specific ELISA.

FIG. 4 presents results concerning the induction and re-repression of hEGF expression in pCEP4-tetR-hEGF-94 in a stably transfected 293T cell line. Panel A: Three weeks after pCEP4-tetR-hEGF-94 transfection and hygromycin B selection, 293T cell pools were seeded at $5 \times 10^4$ cells per well in six-well plates. After 24 h incubation, cells were grown in the presence and absence of tetracycline. Medium was changed and collected every 24 h for 5 days. Panel B: Cells described in panel A were grown in the presence of tetracycline for 24 h. After removal of extracellular medium and washing with DMEM three times, cells were re-grown in the absence of tetracycline for an additional 5 days and medium was collected and changed daily. hEGF concentrations in daily collected medium were determined and presented as means+/− SD. Fold of regulation in hEGF expression are indicated at the top of the bar (A).

DETAILED DESCRIPTION OF THE INVENTION

The present invention is based upon the development of a modified hCMV promoter that is capable of promoting transcription from genes on both strands of DNA. The sequence of such a bidirectional promoter is shown as SEQ ID NO:1 and may be obtained by ligating a sequence that is complementary to a portion of the 3' end of the wild type hCMV sequence to the 5' end of the wild type sequence in reverse orientation. The bidirectional promoter may be used as part of a double stranded sequence that also includes sequences for a tet operator and a tet repressor.

In preferred embodiments gene expression from the promoter is controlled by putting the gene under the control of a tetracycline operator sequence that binds repressor protein to shut off gene expression (for sequences see Postle et al., *Nucl. Acid Res.* 12:4849-4863 (1984); Hillen et al., *Ann. Rev. Microbiol.* 48:345-369 (1994); Wissmann et al., *J. Mol. Biol.* 202:397-406 (1988)). General methods for making recombinant DNA molecules containing these elements and DNA sequences have been previously described (see U.S. Pat. No. 6,444,871) and plasmids which contain the tetracycline-inducible transcription switch are commercially available (T-REx™, Invitrogen, CA).

The tet operator should be located between 6 and 24 nucleotides 3' to the last nucleotide in the TATA element of the promoter and 5' to the gene. The strength with which the tet repressor binds to the operator sequence is enhanced by using a form of operator which contains two op2 repressor binding sites (each such site having the nucleotide sequence: TCCCTATCAGTGATAGAGA (SEQ ID NO:7)) linked by a sequence of 2-20, and preferably 10-13, nucleotides. When repressor is bound to this operator, very little transcription of the associated gene will occur. If DNA with these characteristics is present in a cell that also expresses the tetracycline repressor, transcription of the operably linked gene will be blocked by the repressor binding to the operator. However, if tetracycline is introduced, it will bind to the repressor, cause it to dissociate from the operator, and transcription will proceed.

EXAMPLES

The current example describes the development of a bidirectional hCMV promoter system. A plasmid was constructed in which a sequence coding for tetR was put under the control of a full-length hCMV major immediate-early promoter while the reporter gene hEGF was controlled by a tet-O bearing hCMV promoter with different degrees of truncation at the 5'-end of the promoter. It was found that promoters truncated 94 base pairs from the transcription start site were able to effectively promote EGF production and that this production could be regulated using the tet operator/repressor elements.

A. Materials and Methods

Plasmids: pcmvtetO-hEGF expresses hEGF under the control of the tetO-bearing hCMV major immediate-early promoter (Yao, et al., *Hum. Gene Ther.* 9:1939-1950 (1998)). pCEP4-tetR, derived from pCEP4 (Invitrogen), expresses the tetracycline repressor (tetR) under the control of the hCMV immediate-early promoter (Yao, et al., *Hum. Gene Ther.* 9:1939-1950 (1998)).

Cell Culture, Transfection, and Stable Cell Line Selection:

293T, HeLa, U2OS and Vero cells were cultured in Dulbecco's modified Eagle's medium (DMEM) (Sigma) supplemented with 10% fetal bovine serum (Sigma), penicillin (100 units/ml), and streptomycin (100 μg/ml). Transfection of these cells was performed with LipofectAMINE 2000 (Invitrogen) according to the manufacturer's instructions. Stably transfected cells were selected 24 h after transfection by addition of hygromycin B (Sigma) to the medium to a concentration of 200 μg/ml at the initial stage of selection and further cultured with maintained selective pressure at a concentration of 50 μg/ml.

hEGF ELISA:

Expression of hEGF in extracellular medium was determined by hEGF-specific ELISA as described previously (Yao, et al., *Hum. Gene Ther.* 9:1939-1950 (1998)). The concentration of hEGF in the samples was fit to a SOFT max four-parameter standard curve generated by the use of recombinant hEGF (236-EG; R & D systems) in a twofold dilution series ranging from concentrations of 2 to 2000 pg/ml in a volume of 200 μl/well.

B. Results

Construction and Transient Transfection Analysis of hEGF Expression from pCEP4-tetR-hEGF Plasmids:

pCEP4-tetR is a pCEP4-based episomal-replicating plasmid that encodes tetR under the control of the full-length hCMV major immediate-early promoter (Yao, et al., *Hum. Gene Ther.* 9:1939-1950 (1998)). To minimize the potential homologous recombination between the two hCMV major immediate-early promoters in a single plasmid and to maintain efficient levels of gene expression, we used four different 5' primers (Table 1) for PCR cloning the tetO-bearing hCMV major immediate-early promoters, which are positioned at 522, 248, 130, and 94 bp 5' to the transcription start site of the hCMV immediate-early promoter in plasmid pcmvtetO-hEGF.

TABLE 1

Primers used for PCR amplification of tetO-containing hCMV major immediate-early promoter positioned at 522, 248, 130, and 94 bp 5' to the transcription start site.

| Primer | Sequence |
| --- | --- |
| CMV-522 | GACTTGTACA GTTGACATTGATTATTGAC (SEQ ID NO: 8) |
| CMV-248 | GACTTGTACA ACATCTACGTATTAGTCATC (SEQ ID NO: 9) |
| CMV-130 | GACTTGTACA TGGGAGTTTGTTTTGGCACC (SEQ ID NO: 10) |
| CMV-94 | GACTTGTACA CCAAAATGTCGTAACAACTCC (SEQ ID NO: 11) |
| CMV-pA | GACTTGTACA CAGAAGCCATAGAGCCCAC (SEQ ID NO: 12) |

The 3' primer CMV-pA (Table 1) used for the PCR amplification of different hEGF-containing transcription units is located downstream of the Poly A signal in plasmid pcmvtetO-hEGF. The resulting PCR products were cloned into pCEP4-tetR at the BsrG I site, respectively, yielding plasmids pCEP4-tetR-hEGF. The orientation of the PCR products in the resulting recombinant plasmids was verified by restriction enzyme digestion. According to the length of the tetO-bearing hCMV major immediate-early promoter used for directing the expression of hEGF, these plasmids were designated pCEP4-tetR-hEGF-522, pCEP4-tetR-hEGF-248, pCEP4-tetR-hEGF-130 and pCEP4-tetR-hEGF-94. Restriction enzyme analysis revealed that, whereas the two hCMV promoters are positioned in the same direction in pCEP4-tetR-hEGF-130, the tetO-bearing hCMV promoters in pCEP4-tetR-hEGF-522, pCEP4-tetR-hEGF-248, and pCEP4-tetR-hEGF-94 are oriented opposite the hCMV major immediate-early promoter that directs expression of tetR.

Test of the Levels of hEGF Expression and the Efficacy of Achieving Regulated Gene Expression in this Newly Constructed Single Plasmid Systems:

The described four pCEP4-tetR-hEGF plasmids were first transiently transfected into 293T, HeLa, and Vero cells, respectively. Transfection medium was removed 4 h post-transfection followed by addition of normal growth medium either without tetracycline or with tetracycline at a concentration of 1 μg/ml. Extracellular medium was collected every 24 h and hEGF expression in the extracellular medium was determined by ELISA (Table 2).

TABLE 2

Regulation of hEGF expression in transiently transfected 293T, HeLa and Vero cell lines.

| Cell line | Plasmid | Tet(−)(ng/ml) | Tet(+)(ng/ml) | Fold |
| --- | --- | --- | --- | --- |
| | | 0-24 h | | |
| 293T | pCEP4-tetR-hEGF-94 | 2.32 ± 0.50 | 194.5 ± 21.6 | 83.8 |
| | pCEP4-tetR-hEGF-130 | 8.25 ± 1.72 | 428.5 ± 78.4 | 51.9 |
| | pCEP4-tetR-hEGF-248 | 16.2 ± 1.29 | 495.1 ± 64.8 | 30.6 |
| | pCEP4-tetR-hEGF-522 | 20.4 ± 3.18 | 255.5 ± 34.9 | 12.5 |
| HeLa | pCEP4-tetR-hEGF-94 | 4.17 ± 0.23 | 56.5 ± 7.2 | 13.5 |
| | pCEP4-tetR-hEGF-130 | 12.28 ± 2.24 | 69.4 ± 4.5 | 5.7 |
| | pCEP4-tetR-hEGF-248 | 11.29 ± 1.38 | 72.7 ± 11.6 | 6.4 |
| | pCEP4-tetR-hEGF-522 | 10.53 ± 1.80 | 85.3 ± 12.1 | 8.1 |
| Vero | pCEP4-tetR-hEGF-94 | 0.04 ± 0.01 | 10.90 ± 1.5 | 272.5 |
| | pCEP4-tetR-hEGF-130 | 0.36 ± 0.04 | 12.61 ± 1.6 | 35.0 |
| | pCEP4-tetR-hEGF-248 | 0.72 ± 0.11 | 16.5 ± 1.5 | 22.9 |
| | pCEP4-tetR-hEGF-522 | 0.60 ± 0.08 | 22.9 ± 2.8 | 38.2 |
| | | 24-48 h | | |
| 293T | pCEP4-tetR-hEGF-94 | 8.35 ± 1.27 | 6570 ± 722 | 787 |
| | pCEP4-tetR-hEGF-130 | 19.55 ± 2.42 | 7970 ± 715 | 408 |
| | pCEP4-tetR-hEGF-248 | 20.25 ± 2.47 | 9935 ± 1093 | 491 |
| | pCEP4-tetR-hEGF-522 | 55.60 ± 6.18 | 5450 ± 829 | 98 |
| HeLa | pCEP4-tetR-hEGF-94 | 4.12 ± 0.67 | 435.8 ± 27.4 | 106 |
| | pCEP4-tetR-hEGF-130 | 10.85 ± 2.01 | 455.1 ± 63.6 | 42 |
| | pCEP4-tetR-hEGF-248 | 9.95 ± 1.38 | 467.6 ± 50.7 | 47 |
| | pCEP4-tetR-hEGF-522 | 17.55 ± 2.8 | 437.5 ± 78.2 | 25 |
| Vero | pCEP4-tetR-hEGF-94 | 0.03 ± 0.00 | 295 ± 34 | 9833 |
| | pCEP4-tetR-hEGF-130 | 0.21 ± 0.03 | 390 ± 37 | 1857 |
| | pCEP4-tetR-hEGF-248 | 0.22 ± 0.02 | 363 ± 41 | 1650 |
| | pCEP4-tetR-hEGF-522 | 0.45 ± 0.05 | 327 ± 45 | 727 |

293T, HeLa and Vero cells seeded in 6-well plates were transfected with plasmids pCEP4-tetR-hEGF-94, -130, -248 and -522, respectively. At 4 h post-transfection, medium was changed either in the absence or in the presence of tetracycline at concentration of 1 μg/ml. Extracellular medium was collected every 24 h and levels of hEGF in the extracellular medium was determined by ELISA.

The degree of tetracycline-regulated hEGF expression was markedly higher at 24 to 48 h post-transfection than at 0 to 24 h post-transfection. Among the four different lengths of the tetO-bearing hCMV immediate-early promoters that drive the expression of hEGF, pCEP4-tetR-hEGF-94 yields the most effective tetracycline-dependent regulation of gene expression in 293T cells, HeLa cells, and Vero cells. Close to 10,000-fold of regulated gene expression was observed in pCEP4-tetR-hEGF-94 transfected Vero cells. Notably, unlike previously published studies, which showed that levels of gene expression from hCMV major immediate-early promoter are influenced by the extent of the distal promoter elements, a similar level of hEGF expression was observed in cells transfected with pCEP4tetR-hEGF-94 and pCEP4-tetR-hEGF-522. Because the enhancer element can function in an orientation-independent manner and in distances, the high level of hEGF from the truncated tetO-bearing hCMV-94 promoter (FIG. 2) is likely the result of a cis-acting effect of the hCMV enhancer elements present in the adjacent full-length hCMV major immediate-early promoter that directs the expression of tetR.

Figure 3:
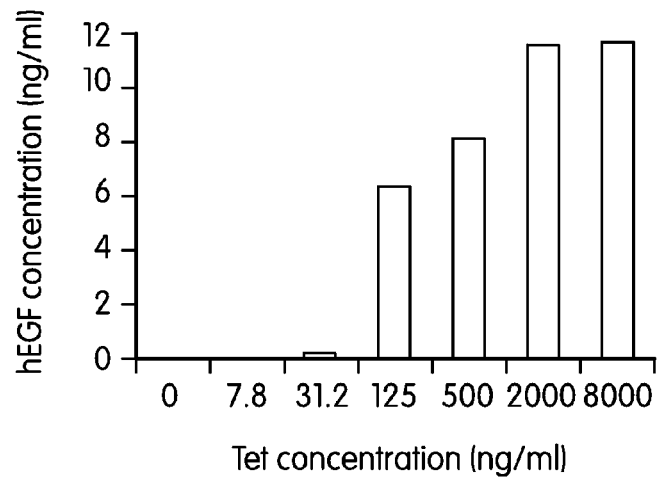

The Effects of Tetracycline Concentration on Gene Expression:

To assess a tetracycline dose-dependent regulation of gene expression from pCEP4-tetR-hEGF, we transfected Vero cells with pCEP4-tetR-hEGF-94. Medium was changed 4 h after transfection followed by addition of fresh medium either with or without tetracycline at various concentrations. FIG. 3 shows that hEGF expression can be sensitively regulated by tetracycline in a dose-dependent manner at concentrations ranging from 21 pg/ml to 11,550 pg/ml. It is evident that the regulation of gene expression by tetracycline is quantitative and that the tetracycline concentrations that yield the most sensitive control of gene expression are between 31.2 ng/ml and 2 μg/ml.

Regulation of Gene Expression in Stably Transfected Cells

Figure 4A:
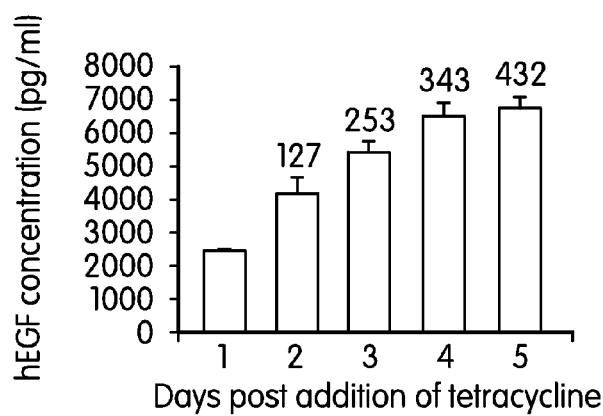

We next assayed tetracycline-regulatable gene expression from hygromycin B resistant colony cells derived from HeLa and 293T cells stably transfected with pCEP4-tetR-hEGF. Of 10 stable colonies randomly picked from pCEP4-tetR-hEGF transfected cell lines, 50% of HeLa cell clones and 100% of 293T cell clones showed tetracycline-inducible hEGF expression. FIG. 4A represents the induction kinetics of hEGF expression from a pool of hygromycin B resistant colonies from 293T cells (293T-4R/EGF cells) stably transfected with pCEP4-tetR-hEGF-94, in which 293T-4R/EGF cells were seeded and grown in the absence and presence of tetracycline (1 μg/ml) for 5 days. Levels of hEGF in daily collected medium was determined by ELISA. 300- to 400-fold of tetracycline-induced hEGF expression was detected on days 4 and 5 post-addition of tetracycline.

Figure 4B:
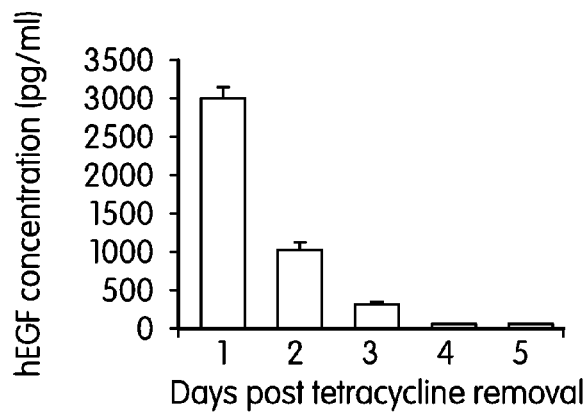

To test whether induction of hEGF gene expression from the stable lines can be reversed following removal of tetracycline, we treated 293T-4R/EGF cells the same as those described in FIG. 4A in six-well plates with tetracycline for 24 h at a concentration of 1 μg/ml and then washed and grew them in the absence of tetracycline for an additional 5 days (FIG. 4B). As a negative control, 293T-4R/EGF cells were seeded as above but received no tetracycline for 6 days. To monitor the re-repression kinetics of hEGF expression, extracellular medium was collected and changed every 24 h. The results show that in contrast to the increased hEGF expression detected from cells that received tetracycline continuously (FIG. 4A), removal of tetracycline led to a significant reduction in hEGF expression starting day 2 post-depletion of tetracycline. On day 5, levels of hEGF expression were decreased to almost the background level of hEGF detected in mock-tetracycline treated control cells (FIG. 4B).

C. Discussion

Figure 1A:
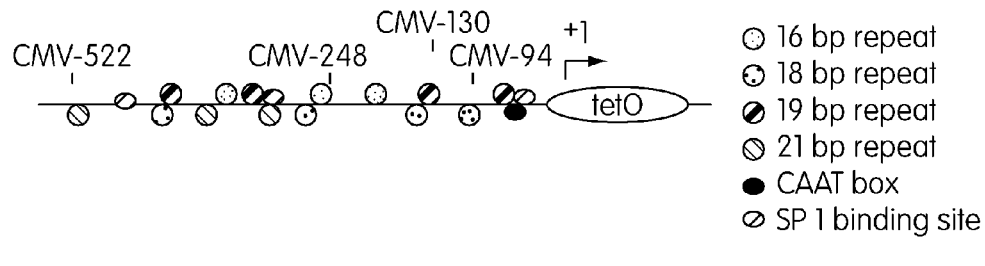
FIG. 1 is a schematic diagram of the tetO-bearing hCMV major immediate-early promoter (A) and plasmids, pCEP4tetR-hEGF (B). Cis-acting elements within the hCMV major immediate-early promoter ($P_{hcmv}$), which interact with (SEQ ID NO: 5)
gagctcgtcgacga*tctctatcactgatagggagatctctatcactgataggga*gagctctgcttatatagacctcccaccgtaca cgcctaccgcccatttgcgtcaatggggcggagttgttacgacattttggaaagtcccgttgattttggTGTACATTTATAT TGGCTCATGTCCAATATGACCGC<u>CATGTTGACATTGATTATTGACTAGTTATTAA</u>
Figure 1B:
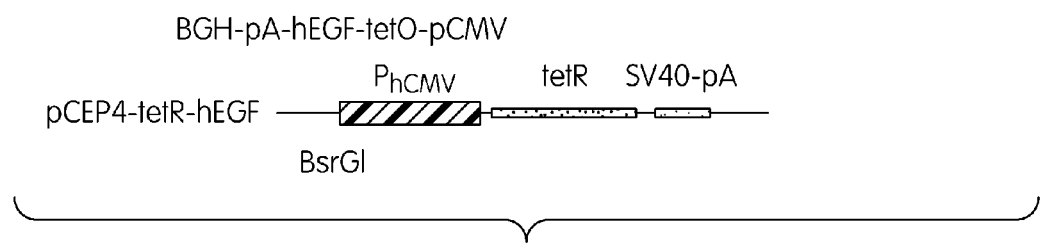

We constructed a set of pCEP4-based constructs encoding tetR under the full-length of hCMV major immediate-early promoter while the reporter gene hEGF was controlled by the tetO-bearing hCMV promoter with different degree of truncations at the 5'-end of the tetO-bearing hCMV major immediate-early promoter. As shown in Table 2, the CMV-94 promoter yielded a high degree of regulated gene expression. While similar levels of hEGF expression were detected among four indicated promoters in an induced state (T+), pCEP4-tetR-hEGF-94 yielded the lowest basal level hEGF expression in the absence of tetracycline. Close to 10,000-fold tetracycline-regulated gene expression was detected in transiently transfected Vero cells. We have further demonstrated that levels of gene expression in transfected cells can be finely adjusted in a tetracycline dose-dependent manner. Collectively, the results from transient transfection assays of Vero cells, 293T cells, and HeLa cells demonstrate that the promoter settings present in pCEP4-tetR-hEGF-94 (FIG. 1) can offer both high and sensitively regulated gene expression in these cells.

We next investigated the efficiency of this newly developed single T-REx-encoding episomal plasmid for the establishment of stable tetracycline-regulatable cell lines in mammalian cells. We observed that 50% of hygromycin B-resistant clones derived from transfected HeLa cells and 100% of hygromycin B-resistant clones from transfected 293T cells exhibit tetracycline-dependent gene expression. It is noteworthy that, since no mammalian cell-transactivating or -repressing domain is needed to achieve regulated gene expression in T-REx, the potential cytotoxicity associated with T-REx during the establishment of regulatable stable cell lines should be minimal as compared with that of the tTA and/or rtTA systems. This unique property should contribute to a high percentage of positive clones and relatively stable established clones for a prolonged analysis of on-and-off regulated gene expression, which could be particularly important for functional analysis of gene function in primary cells and stem cells.

In conclusion, we have developed and tested a new strategy for one-step selection of tetracycline-regulatable stable cell clones based on a T-REx-encoding single episomal replication plasmid. This new system should significantly simplify the establishment of stable cell lines in which the gene of interest can be effectively regulated by tetracycline with minimal risk of insertional mutagenesis to the host cells. The described dual promoter system should also significantly ease the incorporation of tetracycline-repressor based gene switch technology into various virus-based vector systems, particularly for viral vectors that have limited packaging capability, such as lentiviral vectors and adeno-associated viral vectors.

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A bidirectional promoter system derived from the hCMV major immediate-early promoter and comprising the structure X-Y-Z or X-Z, wherein:
   X is a sequence that is complementary to 29-130 consecutive nucleotides at the 3' end of SEQ ID NO:2, and is located at the 5' end of Y or Z but in a reverse orientation;
   Y is a nucleotide linker sequence that is not critical to promoter activity and that is 1-200 nucleotides in length; and
   Z comprises 500-604 contiguous nucleotides extending from the start site of transcription of the sequence shown as SEQ ID NO:2 in the 3' to 5' direction and is located at the 3' end of Y or X, terminating at the start site of transcription.

2. The bidirectional promoter system of claim 1, wherein Y is 1-100 nucleotides in length.

3. The bidirectional promoter system of claim 1, wherein Y is 1-40 nucleotides in length.

4. The bidirectional promoter system of claim 1, wherein X is a sequence that is complementary to 80-110 consecutive nucleotides at the 3' end of SEQ ID NO:2, terminating at the start site of transcription.

5. The bidirectional promoter system of claim 1, wherein X is a sequence that is complementary to 94-108 consecutive nucleotides at the 3' end of SEQ ID NO:2, terminating at the start site of transcription.

6. The bidirectional promoter system of claim 1, wherein said promoter is operably linked to a gene located 3' to Z.

7. The bidirectional promoter system of claim 6, wherein Y is 1-100 nucleotides in length.

8. The bidirectional promoter system of claim 6, wherein Y is 1-40 nucleotides in length.

9. The bidirectional promoter system of claim 6, wherein X is a sequence that is complementary to 80-110 consecutive nucleotides at the 3' end of SEQ ID NO:2, terminating at the start site of transcription.

10. The bidirectional promoter system of claim 6, wherein X is a sequence that is complementary to 94-108 consecutive nucleotides at the 3' end of SEQ ID NO:2, terminating at the start site of transcription.

* * * * *